United States Patent
Toth et al.

[11] 3,979,405
[45] Sept. 7, 1976

[54] 2-OXAZOLINE DERIVATIVES

[75] Inventors: István Tibor Tóth; Pál Bite; György Magyar; Eszter Diszler; József Borsy; Andrea Maderspach; István Polgári; Sándor Elek; István Elekes, all of Budapest, Hungary

[73] Assignee: Gyogyszer- es Vegyeszeti Termekek Gyara RT., Budapest, Hungary

[22] Filed: Oct. 16, 1973

[21] Appl. No.: 406,784

[30] Foreign Application Priority Data
Oct. 20, 1972  Hungary............................ GO1222

[52] U.S. Cl. ............................. 260/307 F; 260/516; 260/518 R; 260/518 A; 260/521 R; 260/521 H; 260/465 R; 260/465 E; 260/465 F; 260/465 G; 424/272
[51] Int. Cl.² ........................................ C07D 263/14
[58] Field of Search................................. 260/307 F

[56] References Cited
UNITED STATES PATENTS

| | | | |
|---|---|---|---|
| 2,579,478 | 12/1951 | Djerassi et al. ...................... | 260/243 |
| 3,318,953 | 5/1967 | Wehrmeister...................... | 260/558 |
| 3,637,726 | 1/1972 | Faith ............... | 260/307 F |
| 3,778,445 | 12/1973 | Timmons et al................. | 260/307 F |

OTHER PUBLICATIONS
Pierce et al: C.A. 46, 2491a (1952).

Primary Examiner—Raymond V. Rush
Attorney, Agent, or Firm—Karl F. Ross; Herbert Dubno

[57] ABSTRACT

This invention relates to compounds of the formula

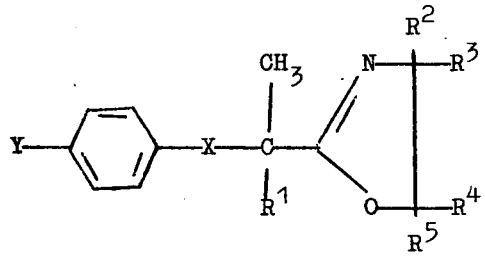

wherein
R¹ is hydrogen or an alkyl group having 1–4 carbon atoms;
R² but R³ are hydrogen and if both R⁴ and R⁵ are hydrogen, R² and R³ are alkyl groups having 1–4 carbon atoms or hydroxymethyl groups;
R⁴ and R⁵ are hydrogen but where both R² and R³ are hydrogen, R⁴ but R⁵ stand for alkyl groups having 1–4 carbon atoms, are amino groups, which may be mono or di-substituted by alkyl groups having 1–4 carbon atoms, or are allyloxymethyl groups;
X is an oxygen or sulphur atom or an NH group;
Y stands for a halogen atom or a halogeno-substituted phenyl group. The disclosure also concerns a process for the preparation of such compounds.

5 Claims, No Drawings

2-OXAZOLINE DERIVATIVES

This invention relates to new 2-oxazoline derivaties, a process for the preparation thereof and pharmaceutical compositions containing the same.

In the prior art a number of 2-oxazoline derivatives are described. Some of these 2-oxazoline derivatives are substituted in position 2 by an alkyl, alkenyl, aralkyl, aralkenyl, aryl or cycloalkyl group, while the other compounds are 2-amino-2-oxazoline derivatives in which the nitrogen atom bears a substituent and partly similar to the above groups. (Chem. Rev., 71, 483; 1971; Angew. Chem. 84, 343; 1972). These known compounds possess fungicidal, antibacterial, central-nerval-system-regulating, anorexigenic, blood-pressure-decreasing, acetyl choline esterase inhibiting and hypoglycaemic properties.

The 2-(biphenyl-methyl)-2-oxazoline derivatives exhibit antiphlogistic activity (Belgian Patent No. 474,100), while the 5-(3,4-dihalogeno-phenoxymethyl)-2-amino-2-oxazolines possess antimicrobial properties (U.S. Pat. No. 3,647,726).

According to the present invention there are provided new 2-oxazoline derivatives of the formula (I)

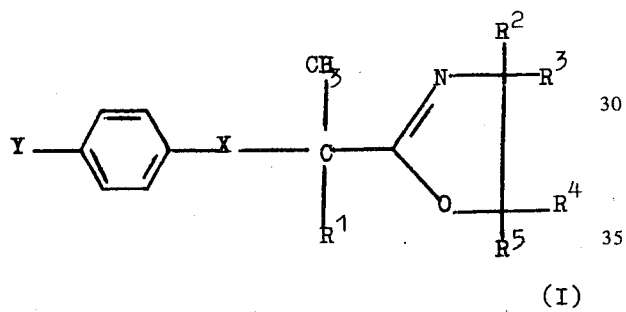

wherein
- $R^1$ is hydrogen or an alkyl group having 1–4 carbon atoms;
- $R^2$ and $R^3$ are hydrogen but where both $R^4$ and $R^5$ are hydrogen, $R^2$ and $R^3$ are alkyl groups having 1–4 carbon atoms or hydroxymethyl groups;
- $R^4$ and $R^5$ are hydrogen but where both $R^2$ and $R^3$ are hydrogen, $R^4$ and $R^5$ stand for alkyl groups having 1–4 carbon atoms, amino groups, which may be mono or disubstituted by alkyl groups having 1–4 carbon atoms, or are allyloxymethyl groups,
- X is an oxygen or sulphur or an NH group;
- Y is a halogen atom or an optionally halogeno-substituted phenyl group).

The new compounds of the formula I differ from the known compounds both in their chemical structure being 2-[aryl(oxy-, thio- or amino)-alkyl]-2-oxazoline derivatives and their therapeutical utility (contrary to the known compounds they exert hypolipemic and hypocholesteric effect).

Preferred representatives of the compounds of the formula (I) are the following derivatives:
2-[(p-chloro-phenoxy)-isopropyl]-4-methyl-4-hydroxymethyl-2-oxazoline;
2-[(p-chloro-phenoxy)-isopropyl]-4-ethyl-4-hydroxymethyl-2-oxazoline;
2-(p-chloro-phenoxy)isopropyl-4,4-bis-hydroxymethyl-2-oxazoline;
2- [-(4'-chloro-phenyl)-phenoxy]-isopropyl -4,4-bis-hydroxymethyl-2-oxazoline;
2- [4-(4'-chloro-phenyl)-phenoxy]-isopropyl -4-methyl-4-hydroxymethyl-2-oxazoline;
2-[-(p-chloro-phenoxy)-butyl-2']-4-methyl-4-hydroxymethyl-2-oxazoline.

According to a further feature of the present inventions there is provided a process for the preparation of compounds of the formula (I)

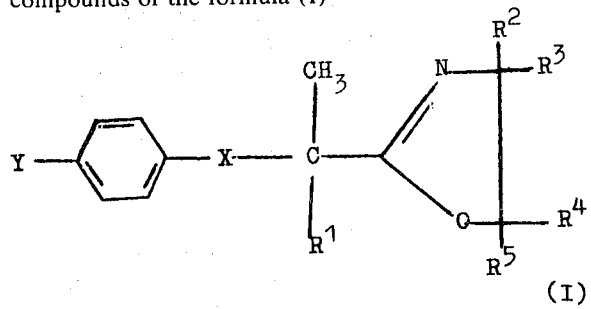

which comprises reacting a compound of the formula (II)

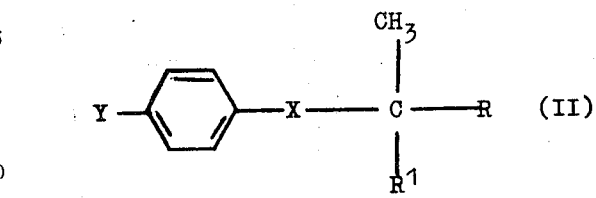

(wherein R is a nitrile or carboxy group and $R^1$, X and Y have the definitions as stated above with the proviso that if X stands for an NH group, R is a carboxy group) with a β-amino-alcohol of the formula (III)

wherein $R^2$–$R^5$ have the definitions stated above.

If a carboxylic acid of the formula (II) is used as starting material, it is preferred to use the β-amino alcohol of the formula (III) in equivalent amount or an excess up to 50%, particularly 10–25% in excess and to cary out the reaction in anhydrous xylene at the boiling point of the reaction mixture. The water formed in the reaction may be continuously removed from the reaction mixture as an azeotropic mixture of xylene and water by using a water separating apparatus. On heating the reaction mixture to boiling for 8–12 hours, the desired product is obtained.

If a nitrile of the formula (II) is used as the starting material, the reaction is preferably accomplished in an anhydrous solvent or in the absence of a solvent. The reaction may be carried out in the presence of a catalyst and at a temperature of 100°–180°C. As solvent an excess (preferably 50–100%) of one of the starting materials (preferably the amino alcohol) or an anhydrous alcohol (such as n-butanol or cyclohexanol) may be used. The catalyst is an alkali alcoholate (preferably sodium methylate or sodium ethylate) or a soluble zinc or cadmium salt (preferably cadmium acetate, zinc acetate or zinc chloride.) The catalyst is used in an amount of 0.03–0.1 mole/mole. In the course of the reaction gaseous ammonia is evolved and the end of the reaction Hs presence is indicated by the termination of the development of ammonia gas.

The starting materials of the formulae II and III are partially known.

The compounds of the formula (II) may be prepared by known methods. (Ber., 52, 89; 1919; Gazz. chim. ital., 36, 334; 1906; Arkiv Kemi, 7, 437; 1954; J. Med. Chem. 12, 1001; 1969). The β-amino-alcohols of the formula (III) may also be prepared by known methods (German Patent No. 718 569, U.S. Pat. No. 2,413,153).

Of the nitriles used as starting material the 2[4-(4'-chlorophenyl)-phenoxy]-2-methyl-propionitrile is a new compound which may be prepared by reacting the corresponding acid amide with phosphorous oxychloride at a temperature between 80°C and 90°C.

In the process of the present invention the following starting materials are preferably used.

Carboxylic acids of the formula II: α-(p-chloro-phenoxy)-propionic acid; 2-(p-chloro-phenoxy)-2-methylpropionic acid;

2-(p-bromo-phenoxy)-2-methyl-propionic acid; 2-(p-chlorophenyl-thio)-2-methyl-propionic acid, 2-(p-chloro-anilino)-2-methyl-propionic acid, 2-[4-(4'-chloro-phenyl)-phenoxy]-2-methyl-propionic acid.

used drug in the field of human cholestrol-reduction therapy) when used in a dose of 300 mg./kg. The compounds of the formula (I) are not toxic and do not show any symptoms of toxicity even when administered in an oral dose of 1000 mg./kg. Thus the therapeutical index of the compounds of the present invention is significantly more favorable than that of Atromid.

The therapeutic activity of the compounds of the present invention is demonstrated by Table I. The following test method was used: male rats weighing 180–200 g. were treated for 10 days with 10, 30, 100 and 300 mg./kg respectively oral doses of the test compound. The animals were used in groups of 10 for each dose. As reference compound Atromid was used in an oral dose of 100 and 300 mg./kg. On the 11 day the animals were bled and the total cholesterol content (Zlatkis, A.; Zak, B.; Boyle, A.J.: Lab. clin. Med. 41, 486; 1953), the triglyceride content (Van Handel, E.: Zilversmit, D.B.: J. Lab. clin. Med. 50, 152; 1957) and the free fatty acid level (Dole, V.P.; clin. Invest. 35, 150; 1956) of the serum was determined. The change of body-weight and liver-weight of the animals and the cholesterol- and triglyceride-content of the liver after extraction was measured (Folch, J.; Lees, M.; Sanley, G.H.: J. biol. Chem. 266, 497; 1957).

The results are demonstrated in Table I/A.

Table I/A

| Compound | Dose mg./kg. p.o. | % change of body-weight | % change of liver weight | % change of serum cholesterol content | % change of serum triglyceride content | % change of serum free fatty acid content | % change of liver cholesterol content | % change of liver triglyceride content |
|---|---|---|---|---|---|---|---|---|
| 2-[2'-(p-chloro-phenoxy)-isopropyl]-4,4-bis-hydroxy-methyl-Δ²oxazoline | 10 | +16.1 | − 5.14 | + 5.9 | −13.4 | +18.2 | +17.6 | + 6.9 |
|  | 30 | +25.6 | − 6.5 | φ | + 3.8 | +13.6 | +12.8 | − 4.3 |
|  | 100 | +19.3 | + 9.5 | −12.3 | −12.6 | −24.3 | +12.7 | −10.1 |
|  | 300 | +11.7 | +31.70 | −38.5 | −44.5 | φ | + 9.7 | −18.8 |
| control |  | +23.5 | — | — | — | — | — | — |
| control |  | +32.1 | — | — | — | — | — | — |
| 2-[2'-(p-chloro-phenoxy)-isopropyl]-4-ethyl-4-hydroxy-methyl-Δ²-oxazoline | 10 | +20.6 | φ | − 0.4 | −44.8 | −19.9 | φ | −17.3 |
|  | 30 | +26.3 | − 1.4 | −10.7 | −37.8 | −20.0 | + 0.7 | −33.2 |
|  | 100 | +22.5 | + 7.9 | −31.3 | −41.3 | + 9.9 | + 8.4 | −27.5 |
|  | 300 | +23.9 | +34.3 | −38.1 | −59.1 | − 9.9 | + 8.7 | −54.2 |
| control |  | +27.0 | — | — | — | — | — | — |
| 2-[2'-(p-chloro-phenoxy)-isopropyl]-4-methyl-4-hydroxy-methyl-Δ²-oxazoline | 10 | +22.2 | + 2.0 | − 4.8 | + 7.8 | +10.1 | +16.3 | +12.5 |
|  | 30 | +25.6 | + 8.0 | − 1.6 | − 7.1 | +16.9 | − 5.8 | −16.7 |
|  | 100 | +26.9 | +32.8 | −23.3 | −29.0 | −11.0 | − 9.4 | + 5.1 |
|  | 300 | +52.8 | +24.5 | −29.0 | −34.9 | + 3.3 | − 4.6 | +10.3 |
| Atromid-S control |  | +20.7 | — | — | — | — | — | — |
| Atromid-S | 100 | +18.8 | +21.6 | − 9.7 | −37.4 | − 6.3 | − 5.1 | −10.7 |
|  | 300 | +12.7 | +49.6 | −17.4 | −37.4 | −31.9 | − 3.8 | −31.9 |

Nitriles of the formula (II): 2-(p-chloro-phenoxy)-2-methyl-propionitrile; 2-(p-chloro-phenoxy)-2-methyl-butyronitrile; 2-(p-chloro-phenylthio)-2-methyl-propionitrile, 2-[4-(4'-chloro-phenyl)-phenoxy]-2-methyl-propionitrile.

Aminoalcohols of the formula III: ethanolamine, 1-amino-2-propanol, 2-amino-1-butanol, 2-amino-2-methyl-1-propanol, 2-amino-2-methyl-1,3-propanediol, 2-amino-2-ethyl-1,3-propanediol, 2-amino-2-hydroxy-methyl-1,3-propane-diol, 1-amino-3-diethylamino-2-propanol, 3-allyloxy-2-oxypropylamine-1.

The new 2-oxazoline-derivatives of the formula (I) possess useful pharmacological activity and may be used as active cholesterol- and lipid level decreasing agents. Thus in a dose of 30–150 mg./kg. they provide the same result as ethyl-2-(p-chloro-phenoxy)-2-methylpropionate (Atromid a wellknown and generally According to the present invention there are also provided pharmaceutical compositions comprising as active ingredient compounds of the formula (I) in admixture with suitable inert nontoxic, solid or liquid carriers. The compositions may be used in solid form (tablets, dragees) or in liquid form (solution, emulsion, suspension). The compositions may be prepared by known methods of the pharmaceutical industry. Usual carriers (e.g. talc, starch, magnesium stearate, calcium carbonate, etc.) may be used. The compositions may optionally comprise additives (e.g. wetting, disintegrating, emulsifying agents, etc.) and other biologically active compounds.

The daily doses may vary within wide ranges and depend on the condition of the patient and the details of the particular case. It is generally preferred to administer the compounds of the formula (I) in a daily amount of from about 300 mg. to about 1.5 g.

A further advantage of the compounds of the formula (I) is their excellent absorption. It is noteworthy that the compounds of the present invention are generally crystalline substances which may be put on the market as tablets or dragees, i.e. in simple dosage unit forms, contrary to the oily Atromide which can be formulated only as pearl capsules.

Further details of the present inventions are to be found in the Examples without limiting the scope of our inventions to the Examples.

EXAMPLE 1

2-[(p-chloro-phenoxy)-isopropyl]-4-ethyl-4-hydroxymethyl-2-oxazoline 19.57 g. (0.1 moles) of 2-(p-chloro-phenoxy)-2-methylpropionitrile are reacted under stirring for 7 hours with 17.88 g. (0.15 moles) of 2-amino-2-ethyl-1,3-propane-diol in the presence of 0.41 g. (0.0075 moles) of sodium-methylate catalyst at a temperature between 140°–150°C. The reaction starts within a few minutes with an intensive development of ammonia gas at this temperature. The end of the reaction is indicated by the cessation of the gas development. After cooling to room temperature the grey-brown coloured oil is dissolved in 200 ml. of chloroform. The chloroform solution is washed with water to neutral reaction, the organic phase is dried on anhydrous magnesium sulphate and the chloroform is distilled off. The remaining oil (26.7 g.) is admixed with 100 ml. of petrolether and the precipitated crystals are filtered out and dried. The raw product obtained (22 g.) is dissolved in 30 ml. of benzene and after the addition of 80 ml. of petrolether the mixture is cooled to −10°C and the precipitated white crystals are filtered. 19.35 g. of the product are obtained. M.p.: 94–95°C.

EXAMPLE 2

2-{[4-(4'-chloro-phenyl)-phenoxy]-isopropyl}-4,4-bis-hydroxymethyl-2-oxazoline 27.17 g. (0.1 moles) of 2-[4-(4'-chloro-phenyl)-phenoy]-2-methyl-propionitrile are reacted under stirring for 10 hours with 18.17 g. (0.15 moles) of 2-amino-2-hydroxy-methyl-1,3-propane-diol in the presence of 0.41 g. (0.0075 moles) of sodium-methylate catalyst at a temperature of 150°–160°C. The reaction takes place under an intensive development of ammonia gas. The reaction finished the reaction mixture is cooled to room temperature, the obtained green-brown coloured resin-like product is dissolved in 120 ml. of hot ethanol, 40 ml. of water are added to the solution, whereupon it is decolorized with charcoal at room temperature. 250 ml. of water are added to the decolorized solution which is cooled to +5°C and the precipitated product is filtered and dried. The dry product (32 g), m.p.: 138°–143°C is purified by recrystallization from ethylacetate. The recrystallized product 22.57 g., yield 60%, has a m.p of 151.5°–152°C.

Preparation of the starting material, the 2-[4-(4'-chlorophenyl)-phenoxy]-2-methyl-propionitrile:

28.98 g. (0.1 moles) of 2-[4-(4'-chloro-phenyl)-phenoxy]-2-methyl-propionamide are reacted under stirring for 3 hours with 25 ml. (0.27 moles) of phosphorous oxychloride at a temperature of 80°–90°C. The reaction takes place under an intensive development of hydrochloric acid gas. When the reaction finished, the mixture is cooled to room temperature and is poured carefully under continual stirring into 200 g. of chopped ice. The ice melted, the precipitated brown-coloured crystalline product is filtered and washed with water to neutral reaction (free from acid). The well-filtered product is dissolved in 150 ml. of anhydrous alcohol, the solution is decolorized at 60°C with charcoal and filtered. 100 ml water are added to the filtrate, then it is cooled in ice-water and the precipitated beige-colored crystals are filtered off and dried. 14.93 g. of the product are obtained (yield 55%), M.p.: 76°–77°C.

EXAMPLE 3

2-[(p-chloro-phenylthio)-isopropyl]-4,4-bis-hydroxy-methyl-2-oxazoline 21.17 g. (0.1 moles) of 2-(p-chloro-phenylthio)-2-methyl-propionitrile are reacted under stirring for 8 hours with 18.17 g. (0.15 moles) of 2-amino-2-hydroxy-methyl-1,3-propanedioliin the presence of 0.54 g. (0.01 moles) of sodium-methylate catalyst at a temperature of 170°–180°C. When the reaction is finished, the mixture is cooled to 25°C and dissolved in 200 ml. of chloroform. The insoluble part is filtered off and the chloroform solution washed with water to neutral reaction. The solution is dried over anhydrous magnesium sulphate and evaporated to dryness. The residue was 25.6 g., mp. 85°–90°C. After recrystallization from a benzene-petrolether mixture 15.8 g. of the product are obtained (yield 50%), mp. 110°–112°C.

EXAMPLE 4

2-[(p-chloro-phenoxy)-isopropyl]-4,4-dimethyl-2-oxazoline 19.57 g. (0.1 moles) of 2-(p-chloro-phenoxy)- 2-methyl-propionitrile are reacted under stirring for 34 hours with 17.83 g. (0.2 moles) of 2-amino-2-methyl-1-propanol in the presence of 0.66 g. (0.003 moles) of zinc acetate catalyst at a temperature of 140°–150°C. The reaction takes place under an intensive development of ammonia gas. When the development is finished, the mixture is cooled, dissolved in 300 ml. of chloroform and the solution washed with water to neutral reaction. After drying the solution over anhydrous magnesium sulphate it is evaporated to dryness. The green-yellow colored oil (26.5 g.), is subjected to fractional distillation in vacuo. The main fraction is a product of 23.6 g. (yield 88%), mp.: 98°–100°C/0.02 mmHg. The distilled product crystallizes after standing for 48 hours, Mp. 59°–61°C.

EXAMPLE 5

The process is as described in Example 4, with the only difference that instead of zinc acetate in the same molecular proportion, zinc chloride catalyst is used. Weight of the product obtained =23 g. (yield 86%).

EXAMPLE 6

The process is as described in Example 4, with the only difference that, instead of zinc acetate in the same molecular proportion, cadmium acetate is used. Weight of the product obtained =23.2 g. (yield 87%).

EXAMPLE 7

The process is as described in Example 1, with the only difference that, instead of sodium-methylate in the same molecular proportion, sodium-ethylate catalyst is used. Weight of the product obtained =19 g. (yield 64%).

EXAMPLE 8

The process is as described in Example 2, with the only difference that, instead of the aminoalcohol, an excess of 10 ml. of n-butanol are used as solvent. Weight of the product obtained =22.18 g. (yield 59%).

EXAMPLE 9

The process is as described in Example 3, with the only difference that, instead of the aminoalcohol- excess 10 ml. of cyclohexanol are used as solvent. Weight of the product obtained =15.15 g. (yield 48%).

EXAMPLE 10–17

The process is analogous to those described in Examples 1 to 6. The data of the compounds prepared are indicated in Table I

EXAMPLE 19

2-{[4-(4'-chloro-phenyl)-phenoxy]-isopropyl}-4-hydroxy-methyl-4-methyl-2-oxazoline 29.07 g. (0.1 moles) of 2-[4-(4'-chloro-phenyl)-phenoxy]-2-methyl-propionic acid and 13.15 g. (0.125 moles) of 2-amino-2-methyl-1,3-propane-diol dissolved in 1400 ml. of anhydrous xylene are boiled for 11 hours in an apparatus provided with a water-separating column. The accumulated water-xylene mixture is occasionally removed from the column. When no more water is leaving the system the boiling is stopped. The xylene is distilled off in vacuo and the partly crystalline partly oily residue is admixed with 300 ml. of ether. After standing for some hours the crystals are filtered off and the ether filtrate is decolorized with active carbon (charcoal) and then evaporated to dryness. The residue is admixed with a cyclohexane-ether mixture (4:1) and after 2 days the precipitated crystals are filtered out. The dried crude product of 17.6 g. has a mp. of 123°–127°C. It is recrystallized from an alcohol-water mixture (4:3). The end-product obtained (10.8 g., yield 30%) has a mp. of 130°–131°C.

Table I.

| Example | $R^1$ | $R^2$ | $R^3$ | $R^4$ | $R^5$ | X | Y | A | B catalyst | C | D | Mp.°C Bp. °C/Hg mm |
|---|---|---|---|---|---|---|---|---|---|---|---|---|
| 10. | —$CH_3$ | H | H | H | H | O | Cl | 40 | 65 | 67 | 70 | 106/0.1 |
| 11. | —$CH_3$ | —$C_2H_5$ | H | H | H | O | Cl | 45 | 67 | 69 | 73 | 130/0.3 |
| 12. | —$CH_3$ | —$CH_3$ | —$CH_2OH$ | H | H | O | Cl | 65 | 75 | 86 | 88 | 71–72 138/0.15 |
| 13. | —$CH_3$ | —$CH_2OH$ | —$CH_2OH$ | H | H | O | Cl | 75 | 73 | 88 | 87 | 141–142 |
| 14. | —$C_2H_5$ | —$CH_3$ | —$CH_2OH$ | H | H | O | Cl | 75 | 76 | 84 | 87 | 135/0.05 |
| 15. | —$CH_3$ | H | H | —$CH_3$ | H | O | Cl | O | 62 | 64 | 71 | 126/0.4 |
| 16. | —$CH_3$ | H | H | —$CH_2N(C_2H_5)_2$ | H | O | Cl | 70 | 75 | 76 | 81 | 140/0.1 |
| 17. | —$CH_3$ | H | H | —$CH_2OCH_2CH=CH_2$ | H | O | Cl | 64 | — | — | — | 148/0.2 |

A=$NaOCH_3$;
B=$ZnCl_2$;
C=$Zn(CH_3COO)_2 2H_2O$;
D=$Cd(CH_3COO)_2 2H_2O$;

EXAMPLE 18

2-[(p-chloro-phenoxy)-isopropyl]-4,4-bis-hydroxy-methyl-2-oxazoline 21.45 g. (0.1 moles) of 2-(p-chloro-phenoxy)-2-methyl-propionic acid and 15.14 g. (0.125 moles) of 2-amino-2-hydroxy-methyl-1,3-propane-diol are boiled for 12 hours in 900 ml. of anhydrous xylol in an apparatus provided with a water-separating column. The water formed during the course of the reaction is accumulated as an azeotropic mixture in the water-separating column from where it is removed from time to time. When no more water is evolved from the system the boiling is stopped. The hot xylene solution is discharged from the insoluble part. After cooling the white crystals precipitated from the xylene solution are filtered off and washed with benzene. After drying, the croude product obtained (21.8 g., Mp. 133°–135°C) is recrystallized from 70% aqueous ethanol. The pure product (12 g., yield 40%) has a mp. of 141.5°–142.5°C.

EXAMPLE 20–25

The process is analogous to that described in Example 18. The data of the compounds prepared are indicated in Table II.

Table II.

| Serial No. of the Example | $R^1$ | $R^2$ | $R^3$ | $R^4$ | $R^5$ | X | Y | Yield % | Mp. °C Bp, °C/mm.Hg. |
|---|---|---|---|---|---|---|---|---|---|
| 20. | $CH_3$— | —$CH_2OH$ | —$CH_2OH$ | H | H | —NH— | Cl | 38 | 116–118 |
| 21. | $CH_3$— | $CH_3$— | —$CH_2OH$ | H | H | O | $C_6H_5$ | 31 | 101–102 |
| 22. | $CH_3$— | —$CH_2OH$ | —$CH_2OH$ | H | H | O | Br | 39 | 130–131.5 |
| 23. | $CH_3$— | $CH_3$— | —$CH_2OH$ | H | H | S | Cl | 42 | 64–66 |
| 24. | $CH_3$— | $C_2H_5$— | —$CH_2OH$ | H | H | S | Cl | 41 | 150–160/1.0 |
| 25. | H | —$CH_2OH$ | —$CH_2OH$ | H | H | O | Cl | 40 | 148–150 |

What we claim is:
1. 2-[(p-chlorophenoxy-isopropyl]-4-methyl-4-hydroxymethyl-2-oxazoline.
2. 2-[-(p-chlorophenoxy)-isopropyl]-4-ethyl-4-hydroxymethyl-2-oxazoline.
3. 2-(p-chlorophenoxy isopropyl)-4,4-bis-hydroxymethyl-2-oxazoline.
4. 2-{[4-(4'-chlorophenoxy-phenoxy]-isopropyl}-4,4-bis-hydroxymethyl-2-oxazoline.
5. 2-[4-(4'-chlorophenyl)-phenoxy]-isopropyl-4-methyl-4-hydroxymethyl-2-oxazoline.

* * * * *

UNITED STATES PATENT AND TRADEMARK OFFICE
CERTIFICATE OF CORRECTION

PATENT NO. : 3,979,405
DATED : September 7, 1976
INVENTOR(S) : Istvan Tibor Toth et al.

It is certified that error appears in the above-identified patent and that said Letters Patent are hereby corrected as shown below:

Claim 4, line 1 (Col. 8, line 64) is to read as follows:

-- 4.  2-{[4-(4'-chlorophenyl)-phenoxy]-isopropyl}- --

Signed and Sealed this

Twenty-fourth Day of October 1978

[SEAL]

Attest:

RUTH C. MASON
*Attesting Officer*

DONALD W. BANNER
*Commissioner of Patents and Trademarks*